United States Patent [19]

Manser

[11] 4,393,199

[45] Jul. 12, 1983

[54] CATIONIC POLYMERIZATION

[75] Inventor: Gerald E. Manser, Cupertino, Calif.

[73] Assignee: S R I International, Menlo Park, Calif.

[21] Appl. No.: 262,935

[22] Filed: May 12, 1981

[51] Int. Cl.$^3$ .................. C08G 65/10; C08G 65/18; C08G 65/20; C07C 43/11

[52] U.S. Cl. .................. 528/408; 260/695; 528/409; 528/417; 528/421

[58] Field of Search ............ 528/408, 417, 421, 409; 260/695; 568/587, 679

[56] References Cited

U.S. PATENT DOCUMENTS

| | | | |
|---|---|---|---|
| 2,792,375 | 5/1957 | Bartelson | 528/408 |
| 3,417,034 | 12/1968 | Hoy | 528/408 |
| 3,558,722 | 1/1971 | Kobayashi et al. | 528/408 |
| 3,850,856 | 11/1974 | Dreyfuss | 528/408 |
| 4,153,786 | 5/1979 | Pruckmayr | 528/408 |

FOREIGN PATENT DOCUMENTS

| | | |
|---|---|---|
| 859643 | 1/1961 | United Kingdom . |
| 882630 | 11/1961 | United Kingdom . |
| 917951 | 2/1963 | United Kingdom . |
| 1023656 | 3/1966 | United Kingdom . |
| 1125935 | 9/1968 | United Kingdom . |
| 1147791 | 4/1969 | United Kingdom . |
| 1192349 | 5/1970 | United Kingdom . |
| 1193924 | 6/1970 | United Kingdom . |
| 1231822 | 5/1971 | United Kingdom . |
| 1232622 | 5/1971 | United Kingdom . |
| 1233299 | 5/1971 | United Kingdom . |
| 1278879 | 6/1972 | United Kingdom . |
| 1380678 | 1/1975 | United Kingdom . |
| 1512528 | 6/1978 | United Kingdom . |
| 2021606 | 12/1979 | United Kingdom . |
| 1575529 | 9/1980 | United Kingdom . |

OTHER PUBLICATIONS

*Journal of Polymer Science*, Part A-1, vol. 9, 265-279, (1971) "Cationic Copolymerization of Tetrahydrofuran with Epoxides".

Gaylord, N. G., *High Polymers*, vol. XIII, Interscience Publishers, Part I, pp. 1-2, 138-139, 189-191 & 303-304.

*Primary Examiner*—Wilbert J. Briggs, Sr.
*Attorney, Agent, or Firm*—Edward B. Gregg

[57] ABSTRACT

Method of carrying out cationic polymerization with molecular weight control in which a preinitiator precursor, e.g. a diol and a catalyst effective for cationic polymerization (or a preformed adduct of such precursor and catalyst) are mixed with a monomer (e.g. a cyclic ether) in proportions of one mol of precursor or adduct and n mols of monomer, where n is the relatively small number of mer units desired in the polymer, causing polymerization to proceed to completion, then treating the resulting living cationic polymer as desired, e.g. quenching with water to introduce a terminal hydroxyl group, adding another monomer to produce a block polymer, reacting with an anionic polymer, etc. Also polymers so formed. Such polymers have low polydispersity and conversion and yield of the desired polymer are high.

8 Claims, No Drawings

CATIONIC POLYMERIZATION

This work was done during the course of Office of Naval Research Contract No. N-00014/79/C/0525.

This invention relates to the cationic polymerization of monomers under conditions to exercize control of molecular weight, and to produce low molecular weight polymers (oligomers) having a relatively low degree of polymerization (e.g. 5 to 30 mer units) and to produce such polymers in high yield and at high conversion and having a low polydispersity.

Certain terms used herein are defined as follows.

Monomers, unless the context indicates otherwise, means a simple molecule, but permissibly a low molecular weight oligomer, which is capable of cationic polymerization.

Catalyst refers to a substance, typified by a Lewis acid, e.g. $BF_3$, which is capable of catalyzing cationic polymerization.

Preinitiator precursor refers to an organic compound which forms, with a catalyst, an adduct or complex (hereinafter called an adduct), such adduct being a preinitiator.

Preinitiator refers to an adduct of an organic compound with a catalyst which results, when brought into contact with a monomer, in the production of an initiating species which starts (initiates) the formation of a chain.

Initiator is the species so formed.

The term "living polymer" is often used herein to indicate the positively charged (cationic) chain resulting from reaction of an initiator with monomer.

The invention will first be described with reference to the polymerization of cyclic ethers as monomers and diols as preinitiator precursors. The invention will then be described in more general terms.

Ordinarily when a cyclic ether such as an epoxide or an oxetane is polymerized, the polymer has a very high average molecular weight unless the reaction is quenched at low conversion, and the product is a mixture having high polydispersity. If the reaction is caused to go to completion, the product predominates in high molecular weight polymers and/or consists of a mixture of polymers of low, medium and high molecular weight.

There is a need for lower polymers (oligomers) of cyclic ethers having well defined molecular weights with low polydispersity and there is a need for a method of producing such polymers.

Heretofore attempts have been reported in the literature of methods purporting to achieve this object. Notable among this literature is a paper by Hammond, Hooper and Robertson in Journal of Polymer Science, Volume 9, pages 265–279 (1971). Hammond and coworkers used propylene oxide, tetrahydrofuran (THF) 1,2-butylene oxide, n-propyl glycidyl ether and mixtures of certain of these cyclic oxides. Such monomers were homo-polymerized or copolymerized and polymerizations were also carried out in the presence of a small amount of 1,4-butanediol. Boron trifluoride etherate was used as the catalyst. Claims are made that the diol was inserted in the polymer molecules and that it facilitated control of polymer molecular weight.

I have found that, upon using 1,4-butanediol and boron trifluoride etherate in ratios suggested by Hammond, either polymerization does not occur or there is no control over molecular weight in the sense of producing, at high conversion and in high yield, a narrow range of polymers having predictable molecular weight and low polydispersity. This is particularly true where one desires to use such a diol in stoichiometric rather than in catalytic proportions to produce a low molecular weight polymer (an oligomer) such as $$HO-R-O-R_1]_n$$

where R represents the organic radical of the diol, $R_1$ represents the organic radical of the cyclic ether and n has a value not greatly exceeding 10 or 30 rather than, say, 50 to 100 or greater.

It is an object of the present invention to provide a method of conducting cationic polymerization of monomers under conditions to produce, in high yield and at high conversion, low molecular weight polymers of low polydispersity.

It is another object of the invention to provide low molecular weight/low polydispersity polymers from monomers which are amenable to cationic polymerization.

The above and other objects will be apparent from the ensuing description and the appended claims.

These and other objects, as will appear, are accomplished in accordance with the present invention by conducting cationic polymerization of a monomer or a mixture of monomers in the presence of a stoichiometric quantity of a preinitiator precursor. By "stoichiometric quantity" is meant a quantity considerably greater than would be needed for catalysis.

In this manner a polymeric product of low degree at polymerization, e.g. 5 to 30, is produced which may be represented by the formula $$I-M]_n^+$$

where I represents an organic group derived from a preinitiator precursor (which in the reaction mixture is initially in the form of an adduct with a catalyst, such adduct being the preinitiator for the reaction); M represents a group derived from the monomer, and n is an integer from, for example, 5 to 30. The subscript n is, of course, an average number but since the product has a low polydispersity, e.g. 1.1 to 1.2, n is close to the molar ratio of the monomer to the preinitiator precursor.

As will appear, the preinitiator precursor leading to I, the monomer leading to M and the catalyst which forms an adduct with the preinitiator precursor may be chosen from large lists of compounds. The requirements for these reactants and catalysts are as follows:

The monomer is one which is susceptible to cationic polymerization.

The preinitiator precursor is a compound which is capable of forming an adduct with a catalyst, such adduct being capable of forming with a molecule of monomer an initiator $$I+M]^+$$

which then adds further monomer units to form a chain $$I+M]_n^+$$

the number of such chains being proportional to (and very nearly equal to) the number of molecules of preinitiator precursor.

The catalyst is effective to catalyse cationic polymerization of the monomer and of forming a preinitiator with the preinitiator precursor.

The principles of the present invention will now be illustrated by the polymerization of cyclic ethers under control of a diol and using boron trifluoride as a catalyst. The particular cyclic ether is the bis(azido methyl) oxetane 3 of Example 5 below and the particular diol is 1,4-butanediol (BDO). These were reacted in molar proportions of 16 mols of the oxetane to one mol of BDO. The catalyst was $BF_3$, which may be mixed first with BDO to form the preinitiator or it may be used in the form of its etherate with diethylether, in which event the BDO displaces the ether to form the preinitiator. In either case a $BDO/BF_3$ adduct is formed which is the preinitiator for the overall reaction $BDO/BF_3$ + n oxetane ⟶

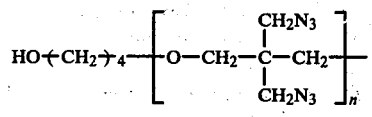

where n is close to 16. Provided conditions are proper, e.g. the mol ratio of BDO to $BF_3$ is approximately 1 mol of BDO to 2 moles of $BF_3$ (i.e., about one mole of $BF_3$ for each hydroxyl of the BDO), a high conversion of the oxetane to polymer occurs, the molecular weight is close to the calculated theoretical molecular weight of 2778 and the polydispersity is low, e.g. about 1.1 to 1.2. Example 6 and Table V below provide experimental details.

In place of BDO other preinitiator precursors such as those of Table I below may be used. In place of the bis(azidomethyl) oxetane, other monomers may be used, such as those described below under the heading "Monomers Other Than Cyclic Ethers". In place of $BF_3$ other catalysts of Table II may be used. General criteria for selection of a preinitiator precursor, monomer and catalyst are as follows. Each will be selected in accordance with the definitions stated above. Note will also be taken of the fact that not all preinitiator precursors of Table I will be operative with all monomers and not all catalysts of Table II will be operative with all preinitiator precursors. Thus if diethylether is the preinitiator precursor of choice and if the reaction is that of its adduct with $BF_3$ with tetrahydrofuran (THF), $BF_3$ may not (and in my experience it does not) function. This does not mean that the $BF_3$/diethylether adduct will not function as a preinitiator for some choice of monomer. Trial and error, coupled with experience and knowledge of the state of the art, will suffice, for a given monomer, to make a proper choice of a preinitiator precursor and a catalyst.

Further guidelines are as follows. If the preinitiator precursor is polyfunctional, e.g. if it is a diol such as BDO, it may be necessary to employ approximately one mol of catalyst for each functional group of the preinitiator precursor to suppress the tendency at free functional groups to terminate a chain prematurely. Also it may be desirable to avoid a large excess of catalyst relatively to the preinitiator precursor to avoid uncontrolled polymerization caused by the free (excess) catalyst.

An illustrative example of choice of a preinitiator precursor is provided by $BF_3$/etherate. As noted, although such an adduct will not, in my experience, result in controlled polymerization of certain monomers, if the ether is displaced by another species of preinitiator precursor such as BDO which binds more strongly to $BF_3$, an effective preinitiator is provided. Therefore, if a species from Table I is considered, it can be determined whether it will displace diethylether from its adduct with $BF_3$. If it will do so, then it is more likely to form a preinitiator with a catalyst from Table III.

General Procedure as Applied to Alcohols as Preinitiator Precursors and Cyclic Ethers as Monomers The following general description, although directed to alcohols as preinitiator precursors and to cyclic ethers as monomers, is applicable to other preinitiator precursors and to other monomers.

(1) The alcohol and the cyclic ether are mixed in the desired molar proportions of 1 mol of alcohol to n mols of monomer, n being, for example 5 to 30. The purpose is to produce predominantly a living polymer $R\text{–}[O\text{–}R_1]_n^+$ If a mixture of cyclic ethers such as

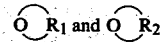

is used the polymer will be an atactic polymer with random distribution of the bivalent groups $\text{–O–}R_1\text{–}$ and $\text{–O–}R_2\text{–}$ unless one of the ethers is much more reactive than the other, in which case one group may predominate in the first segment of the polymer (closer to R) and the other may predominate in the more remote segment of the polymer.

It may be preferred to add the catalyst first to the alcohol and allow time for an alcohol-catalyst adduct (a preinitiator) to form. [See Example 6(c).] A stock of alcohol-catalyst adduct may be prepared and used as needed. The reaction is usually carried out at relatively low temperature, e.g. $-60°$ to $50°$ C. The alcohol and cyclic ether are mixed in stoichiometric proportions to result in the desired polymer $R\text{–}[O\text{–}R_1]_n^+$ where n is the molar ratio of cyclic ether to alcohol. The time required for complete or substantially complete conversion will depend upon the reactants and the catalyst, e.g. three hours is some cases, 24 hours in others. Certain cyclic ethers, e.g. THF, are less reactive and require more time while others such as those of Examples 1 to 7 are more reactive and require less time. Also the reactivity of the alcohol is a factor.

The reaction is carried out in the absence of any substance which would terminate the polymerization reaction. For example, water should be excluded.

When conversion is complete or has been carried to the desired extent (usually complete conversion), the resulting living polymer (a cation) may be treated in various ways such as the following.

Termination. This may be accomplished by adding water to produce a terminal hydroxyl group; by adding ammonia or an amine to produce a terminal amino group, e.g. $NH_2$ (from ammonia) or $\text{–NHCH}_3$ (from methyl amine); by adding a carboxylic acid or its salt to produce a terminal ester group, e.g. an acetate group, CH₃COO—, by adding acetic acid; by adding a mineral acid such as HCl, H₂SO₄ or HF to produce a terminal chlorine, sulfate or fluorine atom or group. In general any terminating species known to terminate a living cationic polymer may be used.

Production of Block Polymers

The living polymer

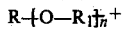

is capable of further polymerization with another cyclic ether species

Hence alternating blocks of —O—R₁, and —O—R₂ may be produced by carrying the first polymerization step to completion, then adding a calculated amount of the second species of ether, etc. to produce an AB type of block polymer:

where the subscripts a, b, c, d—indicate the number of mer units in each block. For example, with THF and oxetane as the cyclic ethers and 1,4-butanediol (BDO) as the alcohol, a polymer

may be produced and may be terminated with water to produce a diol with alternating blocks derived from THF and oxetane. The subscripts a and b may, for example, be 5, 10 or 20 and may be the same or different.

An example of a useful hard (glassy) block polymer which can be used in a thermoplastic elastomer formulation having a $T_m$ (melting point transition temperature) of about 82° C. can be prepared by initiating polymerization of 3,3-bis(azidomethyl) oxetane.

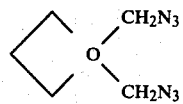

with BDO/BF₃; then when the conversion is complete adding THF, etc. to produce a living polymer containing alternating blocks of mer units derived from the oxetane and THF. The resulting polymer is

R—A—B—A—B - - - X where A represents a block derived from the oxetane and B represents a block derived from THF. R represents the group derived from BDO and X represents a terminating atom or group. This polymer will have useful properties due to the fact that the A blocks have a crystalline (glassy) character while the B blocks are of amorphous (rubbery), character. At temperatures below $T_m$ estimated at about 82° C., the polymer will behave as a highly physically crosslinked elastomer but at higher temperatures it can be molded or extruded to the desired shape, thus behaving as a linear polymer. By reason of the stepwise, controlled addition of A and B blocks the degree of crosslinking, i.e. the crosslinking density, can be controlled. "Crosslinking" as used in this context refers to the forces which cause the A blocks to cluster together and it does not refer to covalent crosslinking.

Copolymerization. Where the polymerization is initiated using a diol such as BDO and the reaction is quenched with water, a diol results such as

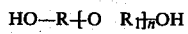

This diol may be employed in any type of polymerization in which diols participate, e.g. in copolymerization with isocyanates to produce polyurethanes and in copolymerization with polycarboxylic acids to produce polyesters.

Specific examples of such copolymers are copolymers of

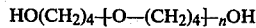

(n=e.g., 5 to 10) with tolylene diisocyanate, and copolymers of the same diol with succinic acid to produce, respectively, a polyurethane and a polyester.

Crosslinking and Control of Crosslinking Density

Under this heading the term "crosslinking" is used to indicate covalent crosslinking between polymer chains caused by polyfunctional groups. Such poly (tri- or higher) functional groups may be present in the preinitiator precursor (e.g. triols and tetrols) or in the monomer (e.g. tri-carboxylic acids) or both.

The polymers of the invention are particularly advantageous in connection with control of crosslinking density. Suppose that a polymer is prepared from, for example, THF or oxetane using the following preinitiator precursors and the following quenching agents.

| Preinitiator Precursor | Quenching Agent | Functionality of Resulting Polymer |
|---|---|---|
| (1) ROH (a monohydric alcohol) | ROH | 0 |
| (2) Same as (1) | H₂O | 1 |
| (3) HOROH (a diol) | ROH (monohydric alcohol) | 1 |
| (4) Same as (3) | H₂O | 2 |
| (5) A triol | ROH | 2 |
| (6) A triol | H₂O | 3 |
| (7) A tetrol | ROH [Same as (1)] | 3 |
| (8) A tetrol | H₂O | 4 |

The functionalities of the resulting polymers will be as indicated in the third column. It is apparent that a polymer can be produced having the desired functionality. If a polymer such as produced according to schemes (4) or (5) is prepared and is copolymerized with a difunctional monomer such as a diisocyanate OCN—R'—NCO or a dicarboxylic acid HOOC—R'—COOH, a linear copolymer will result. If a trifunctional polymer such as is produced according to schemes (6) or (7) is copolymerized with such a difunctional species as a diisocyanate or a dicarboxylic acid, there will be (by reason of the trifunctionality of the polymer) a crosslinking density which may be regarded as 3, representing the trifunctionality of the polymer. By mixing a difunctional polymer such as produced by scheme (4) or (5) with a trifunctional polymer such as produced by scheme (6) or (7), any degree of crosslinking can be obtained ranging from a little more than zero to a crosslinking density of 3. This crosslinking density can be controlled with exactitude.

Other functional groups than OH may, of course, be used such as amino groups introduced as terminators by quenching with ammonia or an amine and will give rise, when copolymerized, to crosslinking densities according to the proportions of difunctional (e.g. one hydroxyl and one amino group per polymer molecule) and trifunctional (e.g. two hydroxyl and one amino group per molecule).

Production of Polymers from di-cations

If the alcohol is a diol in which the hydroxyls are remote from one another, e.g. HO—R—OH where R is a long chain such as —$(CH_2)_8$—, its adduct with a catalyst such as $BF_3$ may be a dication $^+R^+$, e.g. in the case given above,

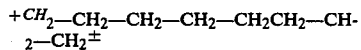

The ends will act with two molecules or monomer to initiate polymerization and will effect molecular weight control to produce a living, di-cationic polymer such as

This living di-cationic polymer may be terminated as in the case of the monocationic living polymers discussed above. Also this di-cationic living polymer may be chain extended by adding a highly polar monomer such as the bisazido monomer of Example 5, then terminating the double chain with water. The resulting polymer may be represented as

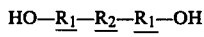

wherein the $R_1$'s are derived from the bisazido monomer and $R_2$ is derived from the dicationic living polymer.

Another type of dication which is amenable to this type of synthesis is described in Smith and Huben U.S. Pat. No. 3,436,359 and British Pat. No. 1,120,304 and is discussed by P. Dreyfuss in a paper in J. Macromol. Science—Chem. A-7 (7), pp. 1361-74 (1973) entitled "Survey of Recent Progress in Polymerization Studies of Selected Heterocycles". This dication together with its counter ions is described by Dreyfuss as having the structure

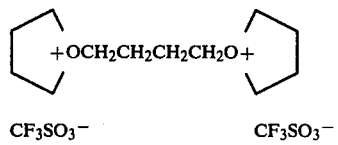

This dication can be employed with a suitable catalyst, e.g. boron trifluoride, to cause polymerization of a cyclic ether to produce a di-cationic living polymer

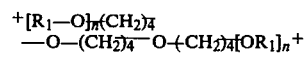

where $R_1$ is derived from the cyclic ether, e.g. THF. This polymer can then be end capped with highly polar groups such as the azido monomer of Example 5 and it can be treated in any of the ways described herein.

Termination by an Anionic Living Polymer. In addition to terminating the cationic living polymer by small groups or atoms as described above, the living cationic polymers may be reacted with a living anionic polymer, e.g. polystyrene living polymer.

In the following Tables I and II suggested preinitiator precursors (Table I) and catalysts (Table II) are set forth.

Table I Preinitiator Precursors

Monohydric alcohols
  Methyl, ethyl and normal and branched chain propyl, butyl, pentyl, hexyl and $C_7$ to $C_{20}$ alkanols
  Cycloaliphatic alcohols such as cyclohexanol and its ring substituted alkyl derivatives
  Aralkyl alcohols such as benzyl alcohol, phenyl ethyl alcohol, di- and tri-phenyl carbinols
  Furfuryl alcohol
Polyhydric alcohols
  Ethylene glycol, propylene glycol, 1,3-propanediol, glycerol, pentaerythritol, 1,4-butanediol; also the diols substituted by functional groups as in the specific examples
Ethers
  Dimethyl, diethyl, di-n and isopropyl ethers; mixed ethers such as methyl ethyl ether;
  Cyclic ethers where not used as monomers, e.g. difficultly polymerizable substituted tetrahydrofurans such as 2-methyl THF
Carboxylic acids
  Formic, acetic, propionic, butyric and other straight and branched chain acids of formula $C_nH_{2n+1}COOH$; aliphatic dicarboxylic acids such as succinic acid
  Aromatic carboxylic acids such as benzoic; o, n and p toluic acids; o, m and p chlorobenzoic acids, phthalic acid, salicylic acid, etc.
Sulfonic acids
  Any of the above acids wherein $SO_3H$ replaces COOH
Esters
  Methyl, ethyl, straight and branched chain $C_3$ to $C_{20}$ alkyl esters of any of the carboxylic and sulfonic acids mentioned above
  Carbonic esters such as diethyl and dimethyl carbonates
Ureas
  Urea, methylol urea, dimethylol urea, other N-substituted ureas

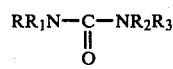

where R, $R_1$, $R_2$ and $R_3$ are selected from H, $C_1$ to $C_{12}$ alkyl, phenyl, benzyl, cyclohexyl, etc., at least one R being an essentially hydrocarbon group
Amides
  Amides of any of the carboxylic acids mentioned above including N-mono- and di-substituted amides

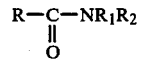

wherein R represents an organic group such as described above and in connection with carboxylic acids, $R_1$ and $R_2$ are selected from H, $C_1$ to $C_{20}$ alkyl, phenyl, benzyl, cyclohexyl, etc.; any of the amides listed in Morrison and Boyd, "Organic Chemistry", 3d ed., page 660, published by Allyn and Bacon, Inc. of Boston
Isocyanates RNCO where R=C₁ to C₁₀ straight and branched chain alkyl, aryl such as phenyl and the tolyl isocyanates Amines C$_1$ to C$_{10}$ straight and branched chain alkylamines; aromatic amines, e.g. aniline; aliphatic cyclic amines, e.g. piperidine; and R—NR$_1$R$_2$ wherein R is an organic group and R$_1$ and R$_2$ are selected from H, straight and branched chain C$_1$ to C$_{10}$ alkyl, aryl (phenyl, o, m and p tolyl) and aralkyl, e.g. benzyl; cycloaliphatic amines, etc.; any of the amines listed in Morrison and Boyd, op. cit., page 729

Acid anhydrides

Anhydrides of any of the carboxylic and sulfonic acids mentioned above; any of those listed in Morrison and Boyd, op. cit., page 660

Ketones

RCOR$_1$ where R and R$_1$ are C$_1$ to C$_{10}$ alkyl, phenyl, benzyl, cyclohexyl; any listed in Morrison and Boyd, op. cit., page 620

Aldehydes

RCHO where R is as defined under "Ketones" above; also any listed in Morrison and Boyd, op. cit., page 620

Analogues of the above

Sulfur, selenium and tellurium analogues of the above may be used, such as:

Thiols, e.g. C$_n$H$_{2n+1}$SH where n=1 to 10

Thioethers, e.g. RS—R$_1$, R and R$_1$ defined as under the heading "Ketones"

Thioacids

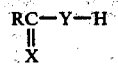

where one or both of X and Y are sulfur, the other, if not sulfur, being oxygen, R being an organic group as under the heading "Carboxylic Acids"

Thioureas—As under the heading "Ureas", doubly bonded O being substituted by S

Thioamides—As under the heading "Amides", doubly bonded O being substituted by S Thioesters—As in "Thioacids" esterified as under "Esters"

Table II Catalysts

Acids generally which are known to be effective for cationic polymerization of tetrahydrofuran and other cyclic ethers, e.g. strong acids and super acids such as
FSO$_3$H
ClSO$_3$H
HClO
HIO
CF$_3$SO$_3$H
Lewis acids such as
AlCl$_3$
BF$_3$
TiCl$_4$
ZnI$_2$
SiF$_4$
SbF$_5$
PF$_5$
AsF$_5$
SbU$_5$ In general any substance known to catalyze cationic polymerization of monomers may be used. Many are described in scientific journals, in texts and in patent literature, e.g. British Pat. No. 1,120,304 to Minnesota Mining and Manufacturing Company and literature referred to in such patent.

Solvents

Any solvent known to be compatible with cationic polymerization as to solubility of reactants, stability of the cation formed on initiation, etc. may be used. Usually it will be a polar aprotic solvent. Examples are:
Methylene chloride
Methyl chloride
Ethylene chloride, ClCH$_2$—CH$_2$Cl
Nitromethane
Chlorinated and fluorinated aromatic hydrocarbons such as chlorobenzene and fluorobenzene Monomers Other Than Cyclic Oxides The cationic polymerization of cyclic ethers, which is described in detail herein, is the best known type of cationic polymerization. The cyclic ethers which are susceptible to this type of polymerization are those having three, four and five membered rings, which are characterized by ring strain. Some of these monomers are difficult or impossible to homopolymerize, e.g. 2-methyl THF. Other classes of monomers susceptible to cationic polymerization include certain vinyl compounds, e.g. isobutylene. Despite the paucity of non-cyclic ether monomers which are susceptible to cationic polymerization, there are such monomers. The method of molecular weight control herein described is applicable to such non-cyclic ether monomers. Reference may be had to texts and journal articles on the subject. One such source is Vol. 37 of Advances in Polymer Science, entitled "Cationic Ring—Opening Polymerization of Heterocyclic Monomers", edited by S. Penczek, P. Kubisa and K. Matyjaszewski, published in 1980 by Springer-Verlag. Cyclic oxides, such as 1,3-dioxalanes having two oxygen atoms in the ring are discussed in this work and may be used as monomers for purposes of the present invention.

The following specific examples will serve further to illustrate the practice and advantages of the invention.

Examples 1 to 3

3-(2,2-dinitropropoxymethyl)-3-methyl oxetane (1) and 2-(2,2-dinitropropyl)-butane-1,4-diol (2) were used as the monomers and boron trifluoride etherate (BF$_3$.Et$_2$O) was used as catalyst. Formulas of 1 and 2 are:

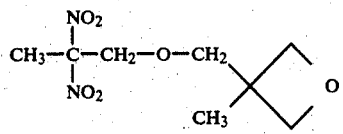

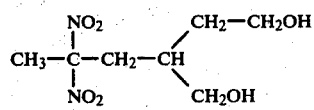

Homopolymerization of 1 using the same catalyst and under varying reaction times and conditions consistently formed polymers of molecular weight 6600. These polymers had a high polydispersity.

By adding stoichiometric amounts of 2 molecular weights could be controlled and predicted and the major fraction of the reaction product in each instance had a low polydispersity. This resulted where stoichiometric ratios of 1 to 2 were 4:1, 6:1 and 8:1. Calculated molecular weights were 1157, 1625 and 2093, respectively, while observed molecular weights were 1200, 1600 and 2000, respectively. The experimental procedure was as follows:

To a flame dried resin flask was added a known weight of cyclic ether as a 20% w/w solution in dried methylene chloride. A calculated weight of the diol was then introduced and the solution stirred at room temperature for 10 minutes. A calculated weight of freshly distilled $BF_3.Et_2O$ was then added and the reaction run for 6 hours. The polymerization was quenched with a volume of saturated aqueous sodium chloride solution equal to the volume of catalyst added. The organic layer was removed, washed with 10% sodium bicarbonate solution and dried over magnesium sulfate.

Example 4 Determination of Mechanism

The diol, represented as (A), may serve as a dication with oxetane molecules (represented as O) adding to both ends, thus

  (1)

Alternatively the initiating cation may be a mono-cation resulting in the structure

A—O—O--- (2)

The oxetane 1 and the diol 2 were mixed in molar proportions of 6 to 1. Reaction was carried out as in Example 1 using the same proportion of catalyst to diol except that the reaction was quenched with an excess (i.e. 2 molar proportions) of the diol. If polymer (1) should result the major product would be

 (1a)

but if polymer (2) should result, the major product would be

A—O—O—O—O—O—O—A (2a)

The major product was determined by gpc, confirmed by nmr analysis for methylene groups, to be 2(a).

If steps are taken to start with a di-cation as described above, the polymer (1a) will result. However with initiating species such as the lower alcohols 2 and 1,4-butanediol, a mono-cation is formed and the polymer (2a) results.

Example 5 Polymerization of Diol 2 with 3,3-Bis(azidomethyl)-oxetane (3)

The formula of 3 is

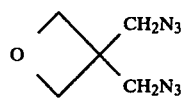 3

It was mixed with 2 and with the same catalyst as in Examples 1 to 4 in molar proportions of one mol of the diol 2 and ten moles of oxetane 3 and with the same catalyst to diol ratio as in Examples 1 to 4. Solvent, reaction time and temperature were as in Examples 1 to 4. The mixture was quenched with water. Calculated molecular weight of the polymer, assumed to be

A—O—O—O—O—O—O—O—O—O—OH (A representing the diol residue, O except for terminal OH representing the group resulting from the oxetane) is 1901. Upon workup as in Examples 1 to 4, 80% of a polymer having a molecular weight of 2200 was recovered. Its polydispersity was 1.1 to 1.2.

Examples 6(a) to 6(f)

The reactants were 1,4-butane diol (4) and the oxetane 3. The procedure was as in Examples 1 to 4 except that in Example 6(c) the diol was added first to the catalyst which was dissolved in a small quantity of methylene dichloride and time (about 2 hours at 20° C.) was allowed for an adduct of catalyst ($BF_3$) and diol to form.

The diol and catalyst were used in different molar ratios and the oxetane and diol were used in the molar ratio of 16:1, calculated to produce a polymer of molecular weight 2778. The reaction was allowed to run for three hours at room temperature and was then quenched with water. The results are set forth in Table III below. Figures in the first three headed columns are mol fractions.

TABLE III

| | Diol | Catalyst (BF₃ Etherate) | Oxetane | Observed Mol. Wt. | Yield, % |
|---|---|---|---|---|---|
| 6(a) | 2 | 1 | 16 | — | 0 |
| 6(b) | 1 | 1 | 16 | — | 0 |
| 6(c) | 1 | 1.5 | 16 | 2900 | 63 |
| 6(d) | 1 | 2 | 16 | 2800 | 68 |
| 6(e) | 1 | 3 | 16 | 3700 | 77 |
| 6(f) | 1 | 4 | 16 | 5000 | 83 |

Commenting upon Table III, no polymerization occurred in 6(a) and 6(b). The oxetane 3 is known to be very reactive, more so than the cyclic ethers of Hammond; hence it was concluded that the lack of reactivity at molar ratios of diol to catalyst in 6(a) and 6(b) is indicative of the need, in the case of a less reactive diol such as 1,4-butanediol, to control its mol ratio to the catalyst. A 2:1 and a 1:1 mol ratio of diol to catalyst were ineffective. A large excess of catalyst as in 6(e) and 6(f) resulted in loss of molecular weight control presumed to be due to the large excess catalyst acting to cause uncontrolled polymerization. A moderate excess[1] of catalyst to diol is indicated. Such close control over alcohol/catalyst mol ratio need not be exercised with more reactive alcohols such as those of Examples 1 to 5. However a large excess of catalyst is preferably avoided.

1. Excess refers to catalyst in excess of one mol per hydroxyl group; that is, in excess of two mols of $BF_3$ per mol of diol.

Yields in Table I were measured on purified product. Polydispersities of product in Examples 6(c) and 6(d) were about 1.1. In Examples 6(e) and 6(f) polydispersities were much higher.

Example 7

The diol 2 and the oxetane 5 [3-(2-fluoro-2,2-dinitroethoxymethyl)-3-methyl oxetane]

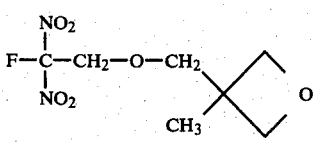

were reacted in varying molar ratios, using boron trifluoride etherate as catalyst under conditions as in Examples 1-4 above and the reaction mixtures were quenched with water. The catalyst was used in the amount of 6.6% by weight based on total monomer. Results are set forth in Table VI.

TABLE VI

| Mols of Oxetane 5 | Mols of Diol 2 | Observed Mol. Wt. | Calculated Mol. Wt. |
|---|---|---|---|
| 4 | 1 | 1200 | 1157 |
| 6 | 1 | 1600 | 1625 |
| 8 | 1 | 2000 | 2093 |

Conversions were 100% and yields were 80-90%. The products had low polydispersity, about 1.1-1.2.

In the course of work done in connection with this invention, certain novel monomers were synthesized. Two such novel monomers, Monomers I and II

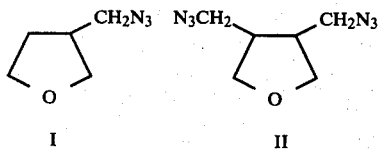

namely 3-azidomethyl THF (I) and 3,4-bisazidomethyl THF (II) were prepared as follows.

Monomer I. Furan-3-methanol was reacted with dihydropyran to produce the tetrahydropyranyl ether. This is a conventional step carried out to protect the hydroxyl group. Other vinyl ethers may be used in place of dihydropyran. The ether was reduced by hydrogen at 1100 psi at 120° C. using a commercially available 56% nickel catalyst. The resulting product was subjected to hydrolysis in acid solution to produce the alcohol III

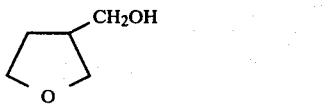

which is believed to be a new compound. The corresponding tosylate was prepared by treatment of III with tosyl chloride and the tosylate was reacted with sodium azide in DMF at 95° C. for 24 hours.

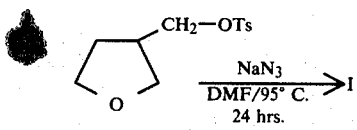

Monomer I was a colorless liquid which, on distillation formed a 1:1 molar complex with DMF which boils at 78° C./15 mm.

Monomer II. Furan-3,4-dimethanol was reduced to 3,4-dimethylol THF which in turn was converted to the ditosylate, such steps being carried out as in U.S. Pat. No. 3,855,237. This ditosylate was treated with sodium azide in DMF at 95° C. for 24 hours.

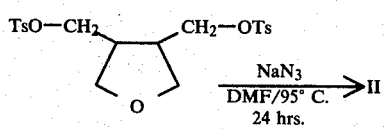

Monomer II was a colorless liquid boiling at 68° C./0.01 mm.

The structures of I and II were confirmed by infra red, nmr and chemical analysis.

I claim:

1. A method of polymerizing a monomer which is capable of cationic polymerization which comprises:
   (a) providing a monomer capable of cationic polymerization
   (b) providing a preinitiator precursor and a catalyst, the catalyst being effective to cause cationic polymerization of monomers, the preinitiator precursor being such that it will form an adduct with the catalyst which in turn will form an initiating species with the monomer which will undergo chain extension with a further quantity of the monomer,
   (c) forming a mixture of the catalyst and preinitiator precursor or separately forming an adduct of the catalyst and preinitiator precursor,
   (d) bringing such mixture or preformed adduct into contact with a quantity of the monomer in the proportion of one mol of adduct to n mols of monomer, n being a relatively small number, the quantity of adduct considerably exceeding the quantity required for catalysis, and
   (e) causing polymerization to proceed to substantial completion, thereby producing a polymer of low polydispersity consisting predominantly of n mer units derived from the monomer and one unit derived from the preinitiator precursor.

2. The method of claim 1 wherein the monomer is a cyclic ether containing 2 to 5 carbon atoms in the ether ring.

3. The method of claim 2 wherein the cyclic ether is an epoxide.

4. The method of claim 2 wherein the cyclic ether is an oxetane.

5. The method of claim 2 wherein the cyclic ether is a tetrahydrofuran.

6. The method of claim 2 wherein the preinitiator precursor is a polyol.

7. The method of claim 6 wherein the preinitiator precursor is a diol.

8. The method of claim 6 wherein the cyclic ether or the polyol or both are substituted by one or more groups that contribute substantially to energy upon decomposition or combustion of the polymer.

* * * * *